(12) United States Patent
Martino-Gauchi et al.

(10) Patent No.: US 7,297,809 B2
(45) Date of Patent: Nov. 20, 2007

(54) CONTINUOUS METHOD FOR PREPARING ETHYL LACTATE

(75) Inventors: Georges Martino-Gauchi, Lyons (FR); Rémy Teissier, Francheville (FR)

(73) Assignee: Arkema France, Colombes (FR)

( * ) Notice: Subject to any disclaimer, the term of this patent is extended or adjusted under 35 U.S.C. 154(b) by 378 days.

(21) Appl. No.: 10/537,150

(22) PCT Filed: Dec. 5, 2003

(86) PCT No.: PCT/FR03/03599
§ 371 (c)(1),
(2), (4) Date: Jun. 2, 2005

(87) PCT Pub. No.: WO2004/052826
PCT Pub. Date: Jun. 24, 2004

(65) Prior Publication Data
US 2006/0014976 A1    Jan. 19, 2006

(30) Foreign Application Priority Data
Dec. 5, 2002    (FR)    .................................. 02 15347

(51) Int. Cl.
C07C 69/66    (2006.01)
(52) U.S. Cl. ..................................... 560/179
(58) Field of Classification Search ...................... None
See application file for complete search history.

(56) References Cited

U.S. PATENT DOCUMENTS

| | | | |
|---|---|---|---|
| 2,406,648 A | 8/1946 | Weisberg et al. | |
| 3,132,079 A * | 5/1964 | Epperly et al. | ............... 203/41 |
| 5,210,296 A | 5/1993 | Cockrem et al. | |
| 5,723,639 A | 3/1998 | Datta et al. | |
| 6,664,413 B1 | 12/2003 | Cockrem | |
| 2002/0004611 A1 | 1/2002 | Eyal et al. | |
| 2003/0008927 A1 | 1/2003 | Fuertes et al. | |

FOREIGN PATENT DOCUMENTS

DE    206373    3/1982

* cited by examiner

Primary Examiner—Paul A. Zucker
(74) Attorney, Agent, or Firm—Steven D. Boyd

(57) ABSTRACT

The invention concerns a continuous method for preparing ethyl lactate by esterifying lactic acid with ethanol, in the presence of a catalyst which comprises reacting said lactic acid with ethanol in an initial ethanol/lactic acid mol ratio not less than 2.5, in the presence of a catalyst, at a reflux of the reaction medium of about 100° C. under absolute pressure ranging between 1.5 to 3 bars. Said method is characterized in that it comprises continuously extracting from the esterification reaction medium a near-azeotropic water/ethanol gas mixture: than dehydrating said gas mixture directly using molecular sieves, than recuperating from said dehydration an ethanol gas stream capable of being recycled to the esterification reaction medium and a flow consisting of water and ethanol which is subjected to distillation wherefrom is obtained water and an azeotropic water/ethanol mixture which is injected into the distillation column head of the gas mixture extracted from the esterification reaction medium; then in continuously extracting crude ethyl lactate which is subjected to purification wherefrom are obtained high purity ethyl lactate and heavy products.

7 Claims, 1 Drawing Sheet

CONTINUOUS METHOD FOR PREPARING ETHYL LACTATE

FIELD OF THE INVENTION

The present invention relates to a process for the preparation of ethyl lactate having a purity of greater than 97% starting from lactic acid or from a lactic acid composition.

BACKGROUND OF THE INVENTION

Ethyl lactate can be used, alone or in combination with other solvents, as cleaning and degreasing agents, in a washing machine and in a nonaqueous medium, for solid surfaces, such as metal components, ceramics, glass or plastics, which have been contaminated by machining oils or greases and/or for their temporary protection.

It can also be used for the defluxing of printed circuits, which operation consists in removing the soldering flux.

The methods most widely used industrially for producing ethyl lactate consist of an esterification reaction generally catalyzed by acids, according to the reaction:

$$CH_3CH(OH)CO_2H + EtOH \rightleftharpoons CH_3CH(OH)CO_2CH_2CH_3 + H_2O \quad (1)$$

However, the implementation of this reaction is complicated due to the presence of a hydroxyl group on the lactic acid molecule.

Esterification can thus take place between two lactic acid molecules and can then continue to give lactic acid oligomers, according to the following schemes:

(II)
(2)

(III)
(3)

or

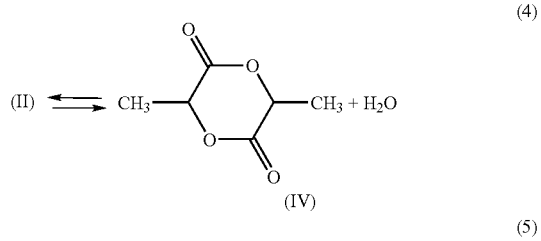
(4)

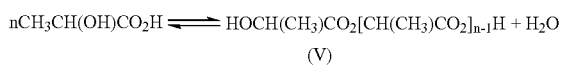
(V)
(5)

According to the operating conditions generally used, the lactide (IV) is not formed. On the other hand, the oligomers (II), (III) and/or (V) have been detected for the good reason that, industrially, commercial lactic acid solutions are used.

The term "lactic acid composition" is understood now to mean any aqueous lactic acid solution, whatever its process of preparation and its characteristics, said solution having a highly variable lactic acid purity.

Commercially available solutions comprising 50, 80, 87 or 90% of organic compounds may in particular be concerned, it being understood that such solutions are in fact mixtures of water, of monomers, of dimers and of higher oligomers of lactic acid.

Thus, in order to productively manufacture ethyl lactate (I), it is necessary not only to esterify the lactic acid monomer but also to depolycondense the oligomers of lactic acid.

Otherwise, oligomers of ethyl lactate are obtained by esterification of the oligomers of lactic acid, according to the reaction:

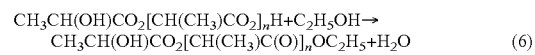
(6)

Consequently, in order to minimize, indeed even eliminate, the formation of the oligomers of ethyl lactate originating from the reaction (6), it is necessary to use a large excess of ethanol and use is generally made of an ethanol/lactic acid molar ratio at least equal to 2.5.

Furthermore, it should be noted that, during the purification of the crude ethyl lactate obtained by esterification of lactic acid with ethanol, a transesterification reaction between two ethyl lactate molecules can occur, according to the reaction:

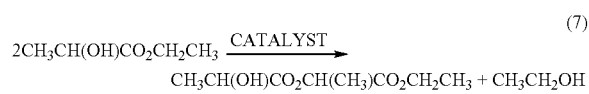
(7)

This transesterification reaction (7) is generally carried out in the presence of basic catalysts, of alkyl orthotitanates or of zirconium-based complexes.

However, it can also take place by heating during the purification of the ethyl lactate and, in order to prevent it, the purification is generally carried out under reduced pressure.

Thus, the esterification of lactic acid to give ethyl lactate is rendered more complicated by:

the presence of oligomers of lactic acid in the starting lactic acid compositions, which it is a matter of depolycondensing in order to obtain the lactic acid, the competition between the expected esterification (lactic acid, ethanol) and two esterifications which result in the formation of ethyl lactate oligomer (one esterification between lactic acid and ethyl lactate, another between ethanol and an oligomer of lactic acid).

In addition, Applicants have found that it is possible to form a water/ethyl lactate binary azeotrope, thus complicating the removal of the water from the ethyl lactate.

It is therefore necessary to produce, during the esterification of lactic acid by ethanol, an ethyl lactate having a water content which is as low as possible in order to subject it to a purification consisting of a distillation under reduced pressure.

Consequently, in order to remove the water formed according to the main reaction (1) and optionally according to the reactions (2) and (3) of the esterification reaction medium comprising a mixture of lactic acid, of ethanol, of ethyl lactate, of water and of oligomers, the simplest method is to use the water/ethanol azeotrope.

However, this results in an ethanol/water mixture which cannot be directly recycled in the reaction medium and, consequently, results in an esterification process which is not very economic industrially.

To achieve this, it is therefore necessary to carry out the separation of the water from the ethanol by a technique other than distillation.

In U.S. Pat. No. 5,723,639, the water is selectively removed from the reaction medium by conveying it through a pervaporation membrane.

However, it is expensive to operate in this way, this operation using a technology not employed to any great extent in the basic chemical industry.

DETAILED DESCRIPTION OF THE INVENTION

Figure 1:
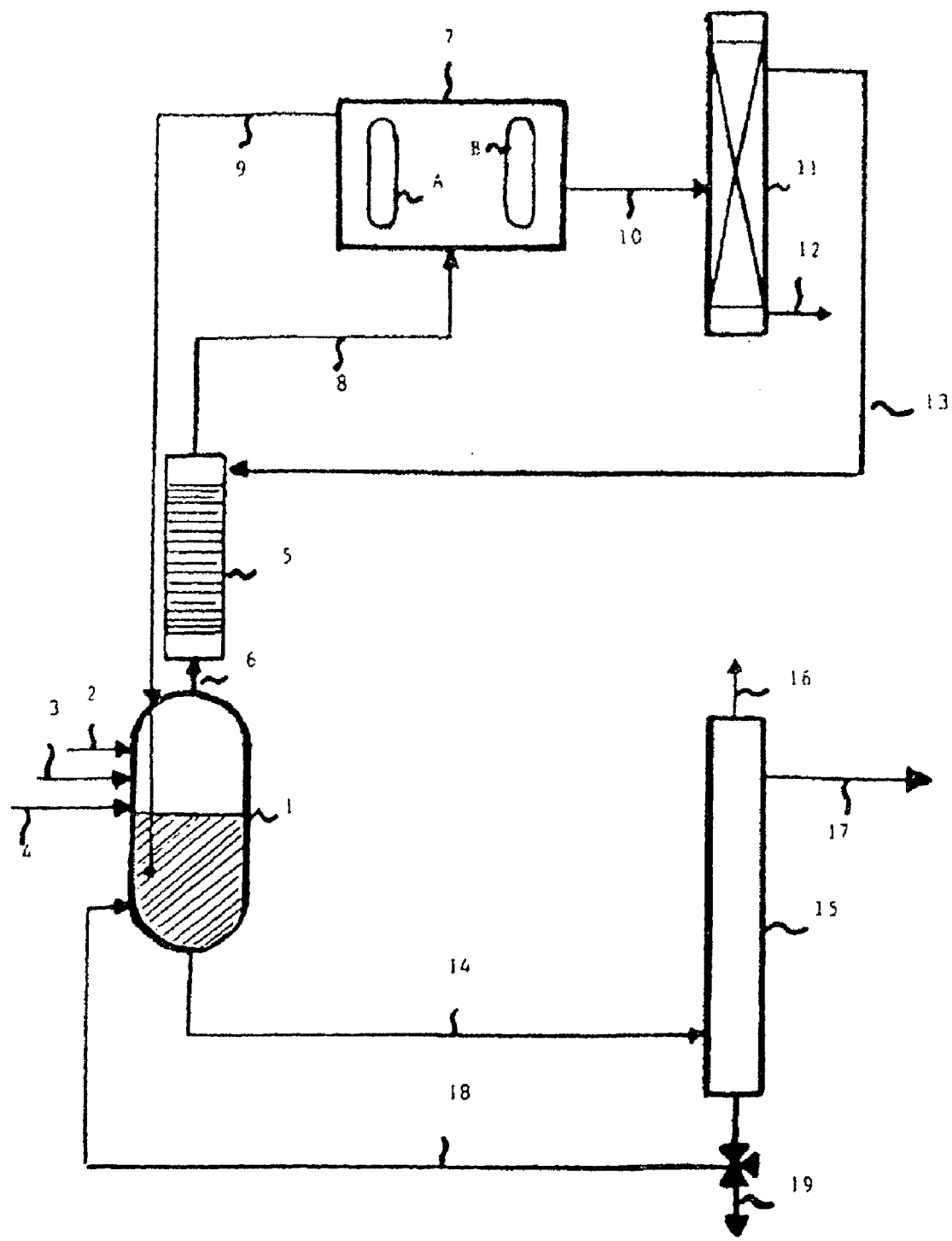
FIG. 1 is a schematic of a device which can be used to carry out the process of the present invention.

Applicants have found that, in a process for the preparation of ethyl lactate by esterification of lactic acid or of a lactic acid composition (as defined above), it is possible to easily and economically remove the water from the esterification reaction medium.

The present invention thus relates to a continuous process for the preparation of ethyl lactate (I) by esterification of lactic acid [or of a lactic acid composition] using ethanol, according to the reaction (1):

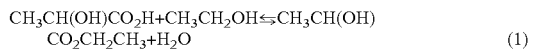

$$CH_3CH(OH)CO_2H + CH_3CH_2OH \rightleftharpoons CH_3CH(OH)CO_2CH_2CH_3 + H_2O \qquad (1)$$

which consists in reacting said lactic acid with ethanol according to an ethanol/lactic acid initial molar ratio at least equal to 2.5 and preferably ranging from 3 to 4, in the presence of a catalyst, at reflux of the reaction medium, which lies at approximately 100° C., and under an absolute pressure ranging from 1.5 to 3 bar and preferably ranging from 1.5 to 1.8 bar; said process being characterized in that a water/ethanol gas mixture close to the azeotrope is continuously extracted from the esterification reaction medium, in that this gas mixture is then dehydrated directly using molecular sieves, in that an ethanol gas stream, which can be recycled to the esterification reaction medium, and a stream composed of water and of ethanol are then recovered from said dehydration, which stream composed of water and of ethanol is subjected to a distillation, from which water and a water/ethanol azeotrope are obtained, which water/ethanol azeotrope is injected at the top of the column for the distillation of the gas mixture extracted from the esterification reaction medium, and in that crude ethyl lactate is then continuously extracted, which crude ethyl lactate is subjected to purification by fractional distillation under reduced pressure, from which an ethyl lactate of high purity and heavy products, which can optionally be recycled to the esterification reaction medium, are obtained.

According to the present invention, the dehydration of the gas mixture extracted from the reaction medium is carried out using the PSA (Pressure Swing Adsorption) technique, which consists in carrying out the selective adsorption of water by passing, at a pressure identical to that applied to the esterification reaction medium, the water/ethanol mixture close to the azeotrope in the gas form through a bed of molecular sieve (adsorption stage) and in then desorbing the water, adsorbed beforehand, by lowering the pressure below 300 mbar and preferably below 100 mbar (desorption stage).

These two stages are carried out alternately.

According to the present invention, the anhydrous ethanol recovered in the adsorption stage is advantageously recycled in the esterification reaction medium, while the water-rich phase is subjected to distillation in order to recover pure water and a water/ethanol azeotrope, which is injected at the top of the column for the distillation of the water/ethanol gas mixture extracted from the reaction medium, thus providing reflux in said column, which is not equipped with a condenser.

The reaction is advantageously carried out in the presence of an acid catalyst which is soluble or insoluble in the esterification reaction medium.

Mention will be made, as examples of soluble catalysts which can be used according to the present invention, of 98% $H_2SO_4$, $H_3PO_4$ or methanesulfonic acid.

Preferably, 98% $H_2SO_4$ will be used.

The catalyst according to the invention is used at molar contents ranging from 0.1% to 4% and preferably at contents ranging from 0.2% to 3%, with respect to the 100% lactic acid employed.

According to the present invention, it is possible to operate in a stirred reactor or using a "fixed bed" technology. In the latter case, solid catalysts, such as ion-exchange resins of the Amberlyst 15 type, will be used.

The initial or start-up time for the esterification can vary to a large extent. It is generally at most equal to 12 hours and preferably between 5 and 12 hours.

The stream of the products exiting from the esterification reaction medium, comprising predominantly ethyl lactate and ethanol, along with traces of water and of heavy products (oligomers), is subjected to fractional distillation under reduced pressure according to the techniques normal to a person skilled in the art.

An ethyl lactate with a purity at least equal to 99% is obtained as top product, and heavy products, which can be recycled in the esterification reaction medium, are obtained as distillation bottom product.

The process according to the present invention can be carried out in a device as represented in FIG. 1.

This device comprises:
- a reactor (1), optionally provided with a stirrer, equipped with temperature probes, with a feed for lactic acid (2), with a feed for ethanol (3) and with a feed for catalyst (4);
- a distillation column (5), devoid of condenser, having between 5 and 15 theoretical plates, fed with gas phase extracted from the reactor (1) via the feed (6);
- a PSA device (7) composed of 2 identical columns (A and B) filled with molecular sieve which operate alternately in adsorption and in desorption; said PSA device, fed with gas phase from the distillation column (5) via the feed (8), is equipped with an outlet (9) connected to the column operating in adsorption which makes it possible to feed the esterification reactor with ethanol (gas) and with an outlet (10) connected to the column operating in desorption which makes it possible to feed a distillation column (11) with water/ethanol mixture; said distillation column (11) is equipped with an outlet (12) for discharging the water and with an outlet (13) for conveying the water/ethanol azeotrope to the top of the distillation column (5);

an outlet for the esterification products (14) feeding a purification region (15) from which the ethanol with water exits via (16), the pure ethyl lactate exits via (17) and heavy products exit via (18), which heavy products can be recycled to the esterification reactor after a bleed at (19).

The process according to the present invention applies very particularly to the esterification by ethanol of the lactic acid present in commercial lactic acid compositions as defined above.

Preferably, use will be made of lactic acid compositions comprising 87% by weight of lactic acid.

The process according to the present invention makes it possible to completely convert the lactic acid of said compositions and to depolymerize the oligomers present in said lactic acid compositions used.

The ethyl lactate originating from the esterification reactor does not comprise much water, which makes it possible to easily purify it.

To operate in the way according to the present invention also makes possible the extraction from the reaction medium of a gas phase virtually devoid of the ethyl lactate formed.

The example which follows illustrates the invention.

EXAMPLE

Preparation of Ethyl Lactate

A test is carried out in a device as represented in FIG. 1. The reactor (1) has a capacity of 2 l.

The PSA system (7) is composed of 2 identical columns (A and B) filled with molecular sieves, Siliporite NK30, 3 Å.

The distillation column is filled with a Sulzer Ex packing with a diameter equal to 20 mm. It has 10 theoretical plates.

The course of the test was as follows:
In a first step, a lactic acid composition is esterified with ethanol under batchwise conditions in the reactor (1). The esterification is carried out at a pressure greater than atmospheric pressure and at a temperature in the region of 100° C.
Then, in a second step, when the degree of conversion of the lactic acid has reached approximately 95%, the esterification reaction is continued continuously in accordance with the present invention according to operating conditions described below.

Batchwise Esterification (Start-Up)

The following are introduced into the reactor (1):
391 g of an 87% lactic acid composition, i.e. 342 g of 100% lactic acid (3.8 mol),
667.4 g of absolute ethanol, i.e. 14.5 mol, which corresponds to an ethanol/lactic acid initial molar ratio equal to 3.81,
3.3 g of 98% $H_2SO_4$ (0.033 mol), i.e. 0.86 mol % with respect to the lactic acid employed.

The reactor is placed under a pressure of 1.5 bar and then the reaction medium is stirred and brought to reflux, which corresponds to a temperature substantially equal to 100° C.

In order to bring the batch to complete conversion (greater than 95%), a gas mixture comprising water and ethanol is continuously extracted from the reaction medium using the distillation column (5), at a column bottom temperature in the region of 100° C. and an absolute pressure equal to 1.5 bar, and then this mixture is dehydrated by conveying it into the PSA system (7) which operates under an absolute pressure of 1.5 bar, from which pure ethanol exits at (9), which ethanol continuously feeds the esterification reaction medium present in the reactor, and from which a water/ethanol mixture exits at (10) during the desorption stage, which water/ethanol mixture is distilled in the distillation column (11), from which a water/ethanol azeotrope exits at (13), which water/ethanol azeotrope is directed to the top of the distillation column (5), thus making it possible to provide reflux at the top of said distillation column. The water exits at (12).

The progress of the reaction is monitored by determining the degree of conversion of the lactic acid, measured by GC.

When the degree of conversion of the lactic acid has reached approximately 95%, which is achieved approximately at the end of 6 hours, the esterification is continued continuously.

The PSA operates in an identical fashion throughout the manufacturing operation.

Continuous Esterification

Then, simultaneously, the esterification reaction medium is fed continuously with:
87% lactic acid composition,
fresh ethanol plus ethanol recycled via (9), while maintaining the fresh ethanol/lactic acid molar ratio in the region of 4,
98% sulfuric acid and heavy products originating from the purification region (15) via (18).

Simultaneously, a mixture comprising ethyl lactate, ethanol, $H_2SO_4$ and traces of water exits via the pipe (14), said crude ethyl lactate being purified by distillation under reduced pressure in the purification region (15).

When the system is operating under stationary conditions, on the one hand the esterification is monitored by analyzing the degree of conversion and the yield of the esterification (by GC) and, on the other hand, the distillation is monitored by analyzing the binary mixture collected as top product from the column (5), which operates with a reflux ratio in the region of 0.27. The residence time is 6 hours.

After the reactor has been replenished 4 times, i.e. operating for 30 hours (including the reaction time under batchwise conditions), a gas mixture having the following composition by weight (mean):
3.9% of water,
96.1% of ethanol, is present at the outlet of the column (5) and a mixture having the following composition by weight (mean):
2.2% of water,
66.3% of ethanol,
27.6% of ethyl lactate,
1.3% of dimer of ethyl lactate, is present at the outlet of the reactor (14).

What is claimed is:
1. A continuous process for the preparation of ethyl lactate (I) by esterification of lactic acid or of a lactic acid composition using ethanol, according to the reaction (1):

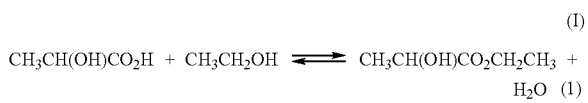

which comprises reacting said lactic acid or lactic acid composition with ethanol at an ethanol/lactic acid initial molar ratio at least equal to 2.5, in the presence of a catalyst, at reflux of the reaction medium, at approximately 100° C., and under an absolute pressure ranging from 1.5 to 3 bar; said process being characterized in that a water/ethanol gas mixture close to the azeotrope is continuously extracted from the esterification reaction medium, in that this gas mixture is then dehydrated directly using molecular sieves, in that an ethanol gas stream, which can be recycled to the esterification reaction medium, and a stream composed of water and of ethanol are then recovered from said dehydration, which stream composed of water and of ethanol is subjected to a distillation, from which water and a water/ethanol azeotrope are obtained, which water/ethanol azeotrope is injected at the top of the column for the distillation of the gas mixture extracted from the esterification reaction medium, and in that crude ethyl lactate is then continuously extracted, which crude ethyl lactate is subjected to purification, from which an ethyl lactate of high purity and heavy products are obtained.

2. The process as claimed in claim 1, wherein the ethanol/lactic acid initial molar ratio ranges from 3 to 4.

3. The process as claimed in claim 1, characterized in that for the dehydration of the gas mixture extracted from the reaction medium using molecular sieve, the Pressure Swing Adsorption technique is used.

4. The process as claimed in claim 3, characterized in that the selective adsorption of water, by passing, at a pressure identical to that applied to the esterification reaction medium, the water/ethanol mixture close to the azeotrope in the gas form through a bed of molecular sieve, and then the desorption of the water adsorbed beforehand, by lowering the pressure below 300 mbar, are carried out alternately.

5. The process as claimed in claim 1, characterized in that the heavy products resulting from the purification of the ethyl lactate are recycled in the esterification reaction medium.

6. The process as claimed in claim 1, characterized in that the absolute pressure ranges form 1.5 to 18 bar.

7. The process as claimed in claim 4, characterized in that the desorption is carried out by lowering the pressure below 100 mbar.

* * * * *